United States Patent
Miller et al.

(10) Patent No.: US 10,024,876 B2
(45) Date of Patent: Jul. 17, 2018

(54) PEDESTRIAN VELOCITY ESTIMATION

(71) Applicant: Apple Inc., Cupertino, CA (US)

(72) Inventors: Isaac Thomas Miller, El Granada, CA (US); Glenn Donald MacGougan, San Jose, CA (US); Robert Mayor, Half Moon Bay, CA (US)

(73) Assignee: Apple Inc., Cupertino, CA (US)

( * ) Notice: Subject to any disclaimer, the term of this patent is extended or adjusted under 35 U.S.C. 154(b) by 368 days.

(21) Appl. No.: 14/732,470

(22) Filed: Jun. 5, 2015

(65) Prior Publication Data

US 2016/0356804 A1   Dec. 8, 2016

(51) Int. Cl.

| | |
|---|---|
| *G01C 21/16* | (2006.01) |
| *G01P 3/00* | (2006.01) |
| *H04W 4/80* | (2018.01) |
| *G01C 22/00* | (2006.01) |
| *G01S 19/19* | (2010.01) |
| *A63B 24/00* | (2006.01) |
| *G01S 19/05* | (2010.01) |
| *H04M 1/725* | (2006.01) |
| *A61B 5/11* | (2006.01) |
| *A61B 5/00* | (2006.01) |

(Continued)

(52) U.S. Cl.
CPC .............. *G01P 3/00* (2013.01); *A61B 5/1118* (2013.01); *A61B 5/1123* (2013.01); *A61B 5/725* (2013.01); *A61B 5/7257* (2013.01); *A63B 24/0062* (2013.01); *G01C 22/006* (2013.01); *G01S 19/05* (2013.01); *G01S 19/19* (2013.01); *H04M 1/72569* (2013.01); *H04W 4/80* (2018.02); *G01S 19/34* (2013.01); *G01S 19/52* (2013.01); *H04M 1/72572* (2013.01)

(58) Field of Classification Search
CPC ......... G01P 3/00; A61B 5/725; A61B 5/1123; A61B 5/1118; A61B 5/7257; H04W 4/008; G01C 22/006; H04M 1/72569; H04M 1/72572; G01S 19/05; G01S 19/19; G01S 19/34; G01S 19/52; A63B 24/0062
USPC ...................................................... 702/151
See application file for complete search history.

(56) References Cited

U.S. PATENT DOCUMENTS

| 5,926,131 A * | 7/1999 | Sakumoto ............... G01S 19/34 342/357.52 |
|---|---|---|
| 9,079,060 B2 | 7/2015 | Hong |
| 2001/0015123 A1 | 8/2001 | Nishitani |

(Continued)

FOREIGN PATENT DOCUMENTS

| CN | 101226061 | 7/2008 |
|---|---|---|
| WO | WO 2013/184493 | 12/2013 |

OTHER PUBLICATIONS

International Search Report and Written Opinion in International Application No. PCT/US2016/020235, dated Jun. 3, 2016, 13 pages.

(Continued)

*Primary Examiner* — Tha-O H Bui
(74) *Attorney, Agent, or Firm* — Fish & Richardson P.C.

(57) ABSTRACT

Systems, methods and computer-readable mediums are disclosed for GNSS velocity estimation for pedestrians. In some implementations, a method includes receiving a periodic sensor signal; determining a fundamental motion frequency of the periodic sensor signal; extracting a periodicity feature from the periodic sensor signal based on the fundamental motion frequency; and responsive to the extracting, initiating pedestrian velocity estimation.

15 Claims, 7 Drawing Sheets

(51) Int. Cl.
   *G01S 19/34* (2010.01)
   *G01S 19/52* (2010.01)

(56) References Cited

U.S. PATENT DOCUMENTS

| | | |
|---|---|---|
| 2012/0271121 A1 | 10/2012 | Della Torre |
| 2012/0274508 A1 | 11/2012 | Brown |
| 2013/0106684 A1 | 5/2013 | Weast |
| 2013/0289932 A1 | 10/2013 | Baechler |
| 2013/0328726 A1* | 12/2013 | Riley .................. G01S 5/02 342/451 |
| 2014/0240567 A1 | 8/2014 | Saito et al. |
| 2015/0073717 A1 | 3/2015 | Hsu |
| 2015/0081061 A1 | 3/2015 | Aibara |
| 2015/0122018 A1 | 5/2015 | Yuen |
| 2015/0371024 A1 | 12/2015 | Kim |
| 2015/0382086 A1 | 12/2015 | Kim |
| 2016/0278700 A1 | 9/2016 | Lee |
| 2016/0287168 A1 | 10/2016 | Patel |

OTHER PUBLICATIONS

Xiao et al., "Robust pedestrian dead reckoning (R-PDR) for arbitrary mobile device placement", 2014 international Conference on indoor Positioning and Indoor Navigation, Oct. 27-30, 2014, 10 pages.

* cited by examiner

PEDESTRIAN VELOCITY ESTIMATION

TECHNICAL FIELD

This disclosure relates generally to pedestrian velocity estimation on mobile devices.

BACKGROUND

Mobile devices are often used with fitness applications for monitoring and tracking fitness-related metrics such as distance walked or run, calorie consumption, and heartbeat. Some mobile devices use velocity data provided by a GNSS receiver that is embedded in or coupled to the mobile device to determine the velocity of a pedestrian user. Power efficient GNSS receivers often run within a short-dwell GNSS power optimization (SDGP) mode. For example, for every second of operation a GNSS receiver may run in full power mode while dwelling on satellite signals (e.g., 200 ms) and then switch to a low power mode for the remaining time (e.g., 800 ms). The difference in power consumption by the mobile device can be significant. The impact of SDGP, however, can lead to errors in the estimate of GNSS velocity.

SUMMARY

Systems, methods and non-transitory, computer-readable storage mediums are disclosed for pedestrian velocity estimation.

In some implementations, a method comprises: receiving a periodic signal; determining a fundamental motion frequency of the periodic signal; extracting a periodicity feature from the periodic signal based on the fundamental motion frequency; and responsive to the extracting, initiating pedestrian velocity estimation.

In some implementations, a system comprises: one or more processors; one or more computer-readable mediums coupled to the one or more processors and configured to store instructions, which, when executed by the one or more processors, causes the one or more processors to perform operations comprising: receiving a periodic sensor signal; determining a fundamental motion frequency of the periodic sensor signal; extracting a periodicity feature from the periodic sensor signal based on the fundamental motion frequency; and responsive to the extracting, initiating pedestrian velocity estimation.

In some implementations, a non-transitory, computer-readable storage medium has instructions stored thereon, which, when executed by the one or more processors, causes the one or more processors to perform operations comprising: receiving a periodic sensor signal; determining a fundamental motion frequency of the periodic sensor signal; extracting a periodicity feature from the periodic sensor signal based on the fundamental motion frequency; and responsive to the extracting, initiating pedestrian velocity estimation.

Particular implementations disclosed herein provide one or more of the following advantages. A periodicity feature extracted from a periodic sensor signal is used to initiate pedestrian velocity estimation to reduce device power usage and improve the accuracy of position and velocity estimates calculated by, for example, a GNSS receiver.

The details of the disclosed implementations are set forth in the accompanying drawings and the description below. Other features, objects and advantages are apparent from the description, drawings and claims.

DESCRIPTION OF DRAWINGS

The same reference symbol used in various drawings indicates like elements.

DETAILED DESCRIPTION

Overview

Figure 1:
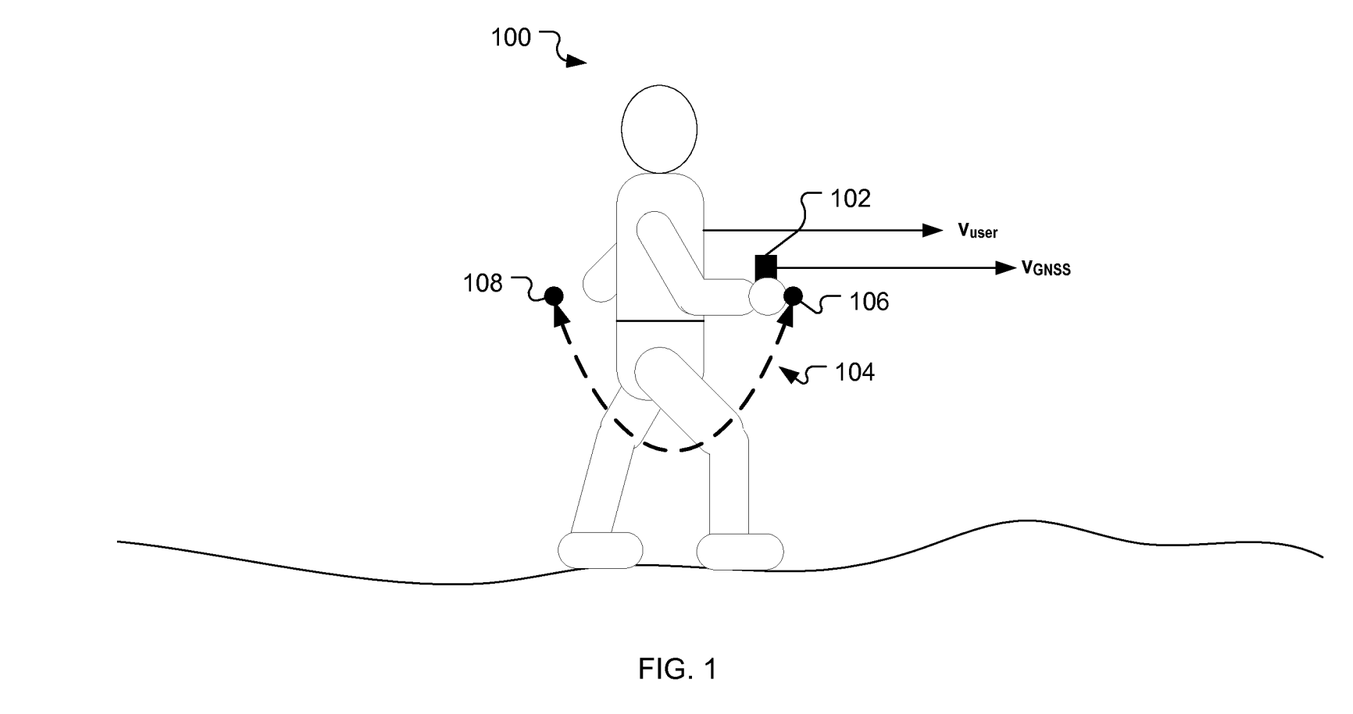
FIG. 1 illustrates the effect of device body location on pedestrian velocity estimation.

FIG. 1 illustrates the effect of device body location on pedestrian velocity estimation. In the example shown mobile device 102 (e.g., a smart phone, wrist watch) is held or worn by user 100. Embedded in or coupled to mobile device 102 is a GNSS receiver, such as a Global Positioning System (GPS) receiver. In some implementations, the GNSS receiver implements a digital phase-lock loop (PLL) to track continuously a carrier frequency of a satellite signal. The difference between the known satellite carrier frequency and the frequency determined at the GNSS receiver is known as Doppler shift. Doppler shift is directly proportional to velocity of the GNSS receiver along the direction to the satellite. With multiple satellites tracked, it is possible to estimate a three-dimensional (3D) velocity vector of the GNSS receiver in a reference coordinate frame, such as Earth-Centered-Earth-Fixed (ECEF) or East-North-Up (ENU). The magnitude or modulus of the velocity vector is the speed of the GNSS receiver and therefore the speed of mobile device 102. The speed estimate can be used to determine a distance traveled by user 100 when mobile device 102 is worn or held by user 100.

To use GNSS velocity estimates for pedestrians, one must deal with the effects of device body location. For example, if mobile device 102 is held in the hand of user 100 as shown, the GNSS receiver may estimate the velocity of the hand rather than the velocity of the body of user 100. The hand of user 100 can be traveling at twice the speed of the body of user 100 or near zero. If satellite tracking locks phase with a certain phase of arm swing path 104, the GNSS velocity estimate can be consistently biased for long periods of time (e.g., 20-60 s).

The magnitude or modulus of an acceleration signal provided by accelerometers of mobile device 102 tends to be periodic when user 100 walks with mobile device 102 in hand because walking is a fundamentally periodic activity. If user 100 is swinging her arm along arm swing path 104, an interesting periodicity feature is the local minimum acceleration magnitude, which occurs twice per arm swing motion: once when the arm swings to apex 106 in front of user 100 and once when the arm of user 100 swings to apex 108 behind user 100. At apexes 106, 108 (the terminus points of arm swing path 104), the estimated GNSS velocity ($V_{GNSS}$) will be approximately equal to the velocity of the user's body ($V_{USER}$). Accordingly, the times when apexes 106, 108 of arm swing path 104 are reached provide desirable times to start GNSS satellite tracking, as described below in reference to FIG. 2.

Example System

Figure 2:
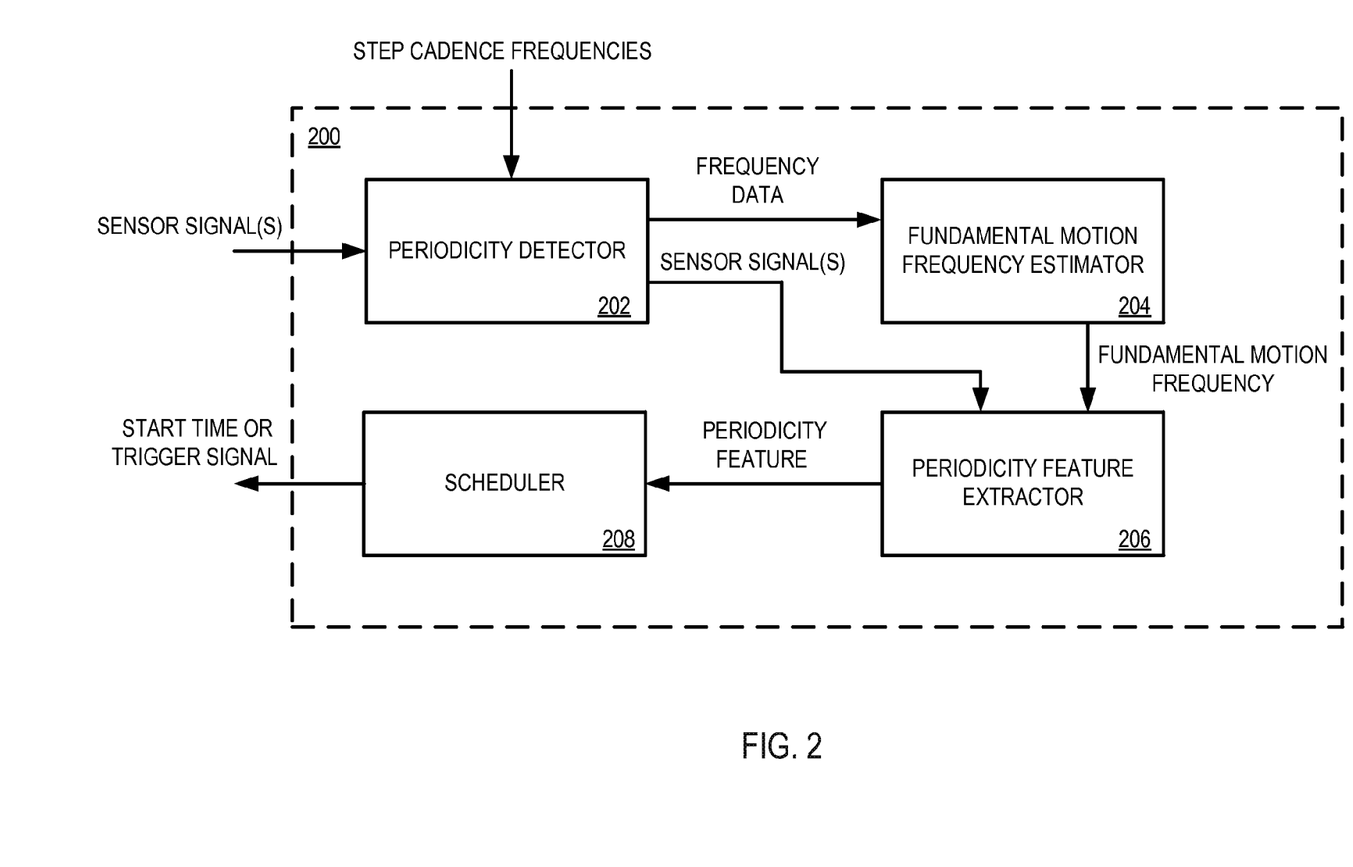
FIG. 2 is a block diagram illustrating an example system for detecting and extracting a periodicity feature from a sensor signal.

FIG. 2 is a block diagram illustrating an example system 200 for detecting and extracting a periodicity feature from a sensor signal. In the example that follows, the sensor signal is an acceleration vector provided by a three-axis accelerometer and the periodicity feature is the local minimum acceleration magnitude. Other sensor signals and periodicity features can also be used such as a gyroscope signal, which can be used to determine the periodic rotation of the arm.

In some implementations, system 200 can include periodicity detector 202, fundamental motion frequency estimator 204, periodicity extractor 206 and scheduler 208. Periodicity detector 202 receives one or more sensor signals and step cadence frequencies. For example, detector 202 can receive an acceleration vector or magnitude. If an acceleration vector is provided detector 202 can calculate the norm of the vector to obtain the magnitude or modulus. In some implementations, detector 202 can pre-process the sensor signal by applying a low pass or band pass filter to remove unwanted frequencies outside the range of frequencies of interest determined by the step cadence frequencies (e.g., 0.45-3.15 Hz). In some implementations, a moving average or median filter can be applied to the sensor signals.

In some implementations, detector 202 can include a sliding window Discrete Fourier Transform (DFT) that is applied to a set of samples of the sensor signal to detect periodicity in the signal. Frequency data generated by detector 202 is provided to fundamental motion frequency estimator 204, which determines the instantaneous fundamental motion frequency. For example, if the length of the sliding window used in detector 202 is approximately equal to the fundamental period of the user's arm swing, the lowest non-zero frequency bin output by the DFT can be selected as the fundamental frequency. In some implementations, an instantaneous fundamental motion frequency can be determined as a weighted average over outlier DFT bin frequencies. In some implementations, the DFT can be implemented using a Fast Fourier Transform (FFT).

The instantaneous fundamental motion frequency can be provided as input to periodicity feature extractor 206, which extracts a periodicity feature from the sensor signal based on the fundamental motion frequency. In this example, where the sensor signal is the acceleration magnitude, the periodicity feature is the local minimum acceleration magnitude. The local minimum acceleration magnitude occurs at apexes 106, 108, as described in reference to FIG. 1. If the fundamental motion frequency is $f_s$, then the fundamental period of the signal is $T_s=1/f_s$ and the local minimum acceleration magnitude occurs every $T_s$ seconds. There may be other local acceleration minima. For example, a pedestrian with a device swinging in his hand tends to reach a local acceleration minimum each time one of the user's feet is as far off the ground as possible. Sometimes the strongest DFT frequency is the user's step frequency (e.g., the frequency of the user's footfalls) and sometimes it is the user's gait frequency (e.g., the frequency of the user's left footfalls).

In some implementations, the observed period signal (e.g., acceleration magnitude) need not be periodic at all times and the fundamental motion frequency may change over time. In these cases, a phase tracking algorithm (e.g., a phase-locked loop (PLL), delay-locked loop (DLL), Kalman filter) can use the fundamental motion frequency to track the phase of the sensor signal so that the periodicity feature can be extracted from the sensor signal.

Scheduler 208 is informed each time the periodicity feature is extracted from the sensor signal. Scheduler 208 is configured to notify one or more subsystems (e.g., a GNSS receiver or chip) when to start pedestrian velocity estimation. This notification can be a trigger signal and/or can include a predicted time of the next periodicity feature extraction. For example, with knowledge of the most recent arm swing apex and the fundamental motion frequency (arm swing motion frequency), the time of the next apex can be predicted and used to schedule pedestrian velocity estimation. Accordingly, pedestrian velocity can be estimated each time the arm swing reaches an apex. At each apex 106, 108, the rotational accelerations are substantially zero and the linear velocity of the body of user 100 becomes the dominant force detected by the accelerometers, as described in reference to FIG. 1.

Figure 3A:
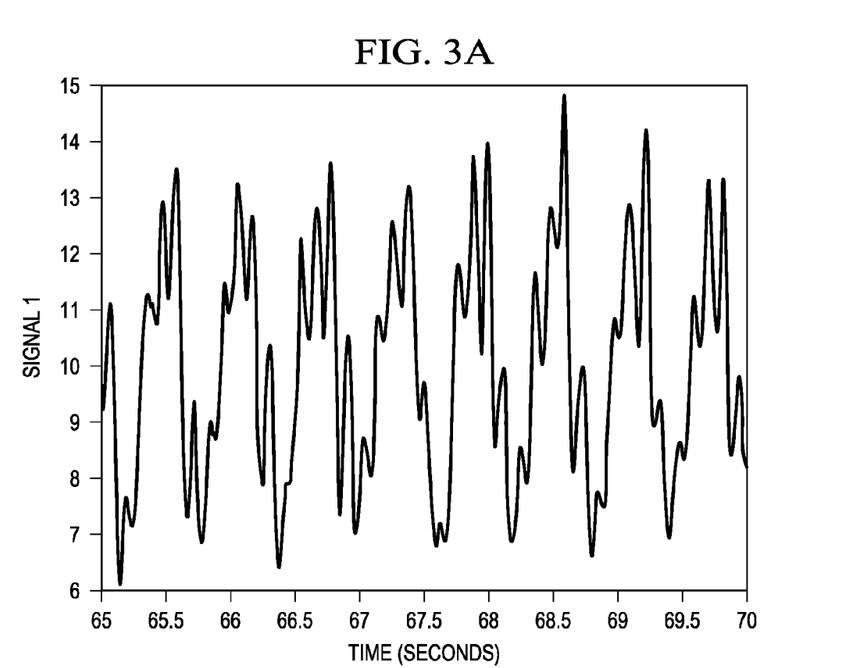
FIGS. 3A-3D are graphs illustrating detecting and extracting a periodicity feature from a sensor signal.
Figure 3B:
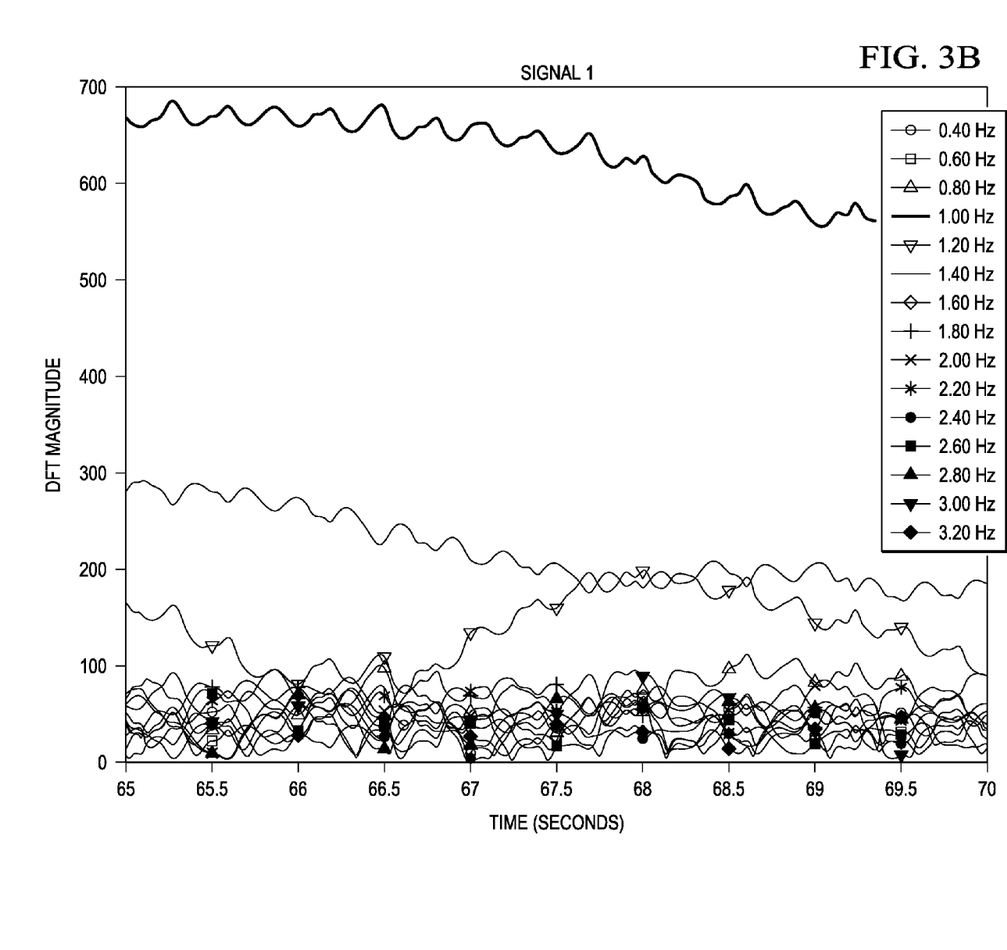
Figure 3C:
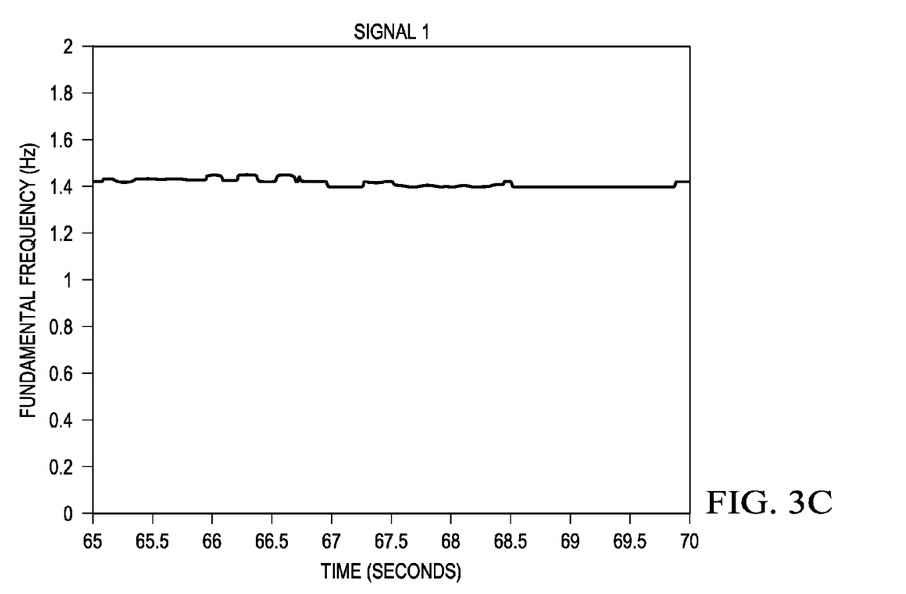
Figure 3D:
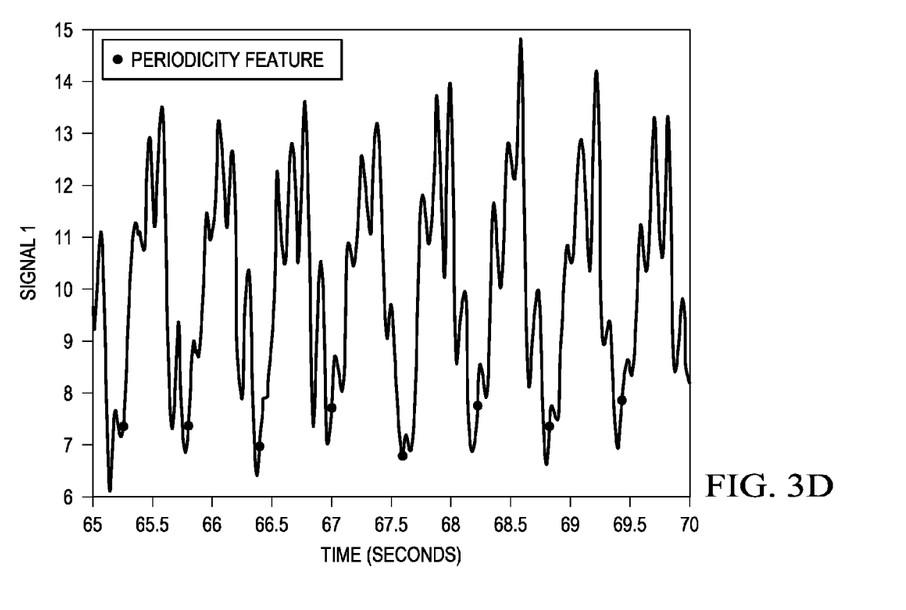

FIGS. 3A-3D are graphs illustrating detecting and extracting a periodicity feature from a sensor signal. FIG. 3A illustrates an accelerometer magnitude in the time domain. A sliding window DFT is applied to the sensor signal and the DFT magnitude as a function of time is shown in FIG. 3B. As can be observed in FIG. 3B, within the sliding window there is an outlier DFT magnitude at around 1.4 Hz. Accordingly, as shown in FIG. 3C, 1.4 Hz is selected as the fundamental motion frequency of the sensor signal in FIG. 3A. FIG. 3D illustrates the use of the fundamental motion frequency to extract the periodicity feature from the acceleration magnitude signal, which in this example is the local minimum acceleration magnitude. A predicted time of the next local minimum acceleration magnitude can be determined and used to initiate or schedule pedestrian velocity estimation, as described in reference to FIG. 2. For example, SDGP can be synchronized to the user's arm swing such that full power GNSS satellite tracking is initiated when the user's arm is at one of its apexes.

Example Process

Figure 4:
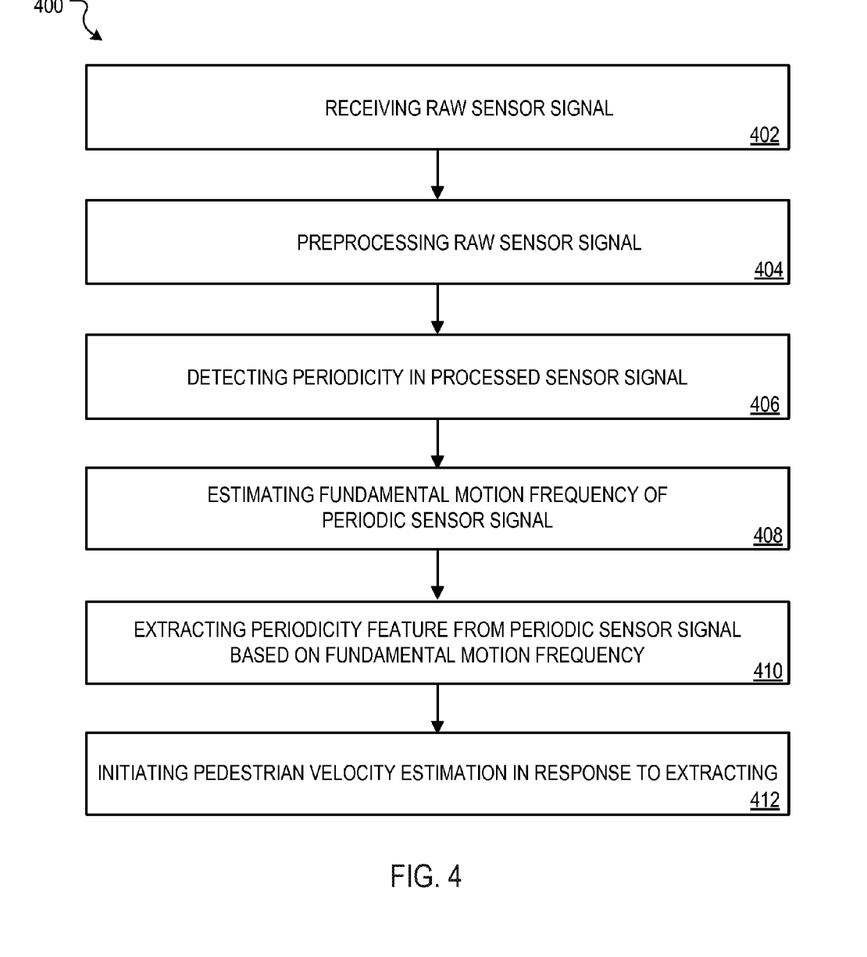
FIG. 4 is a flow diagram of an example process of detecting and extracting a periodicity feature from a sensor signal.

FIG. 4 is a flow diagram of an example process 400 of detecting and extracting a periodicity feature from a sensor signal. Process 400 can be implemented by mobile device architecture 500, as described in reference to FIG. 5.

In some implementations, FIG. 4 can begin by receiving one or more raw sensor signals (402). The signals can be provided by sensors embedded or coupled to a mobile device carried or worn by a user. Some examples of mobile devices include but are not limited to smart phones, computer tablets and smart watches. The sensor can be any sensor that can detect periodic motion including but not limited to accelerometers and gyroscopic sensors.

Process 400 can continue by pre-processing the raw sensor signal (404). For example, pre-processing can include taking a norm of a sensor signal vector and applying a filter to the norm. Some examples of filters include but are not limited to a moving average or median filter. In some implementations, step 404 is optional.

Process 400 can continue by detecting periodicity in the sensor signal (406). For example, a sliding window DFT can be applied to the sensor signal. The window width is based on step cadence frequencies. The step cadence frequencies can be based on averages or other empirical data or provided by the user. In some implementations, the step cadence frequencies can be derived from the user's stride length if known or estimated for various activity motion classes (e.g., walking or running)

Process 400 can continue by estimating a fundamental motion frequency of the sensor signal (408). For example, the lowest non-zero frequency bin output by the sliding window DFT can be selected as the fundamental frequency of the periodic sensor signal.

Process 400 can continue by extracting a periodicity feature from the periodic sensor signal based on the fundamental motion frequency (410). For example, if the sensor signal is acceleration magnitude, the local minimum acceleration magnitude can be the extracted periodicity feature. If the fundamental motion frequency is known, the time of the most recent periodicity feature extraction can be used to predict the time of a next periodicity feature extraction.

Process 400 can continue by initiating pedestrian velocity estimation at the predicted time of the next periodicity feature extraction (412). In some implementations, the time of extraction of the next periodicity feature can generate a trigger signal that is sent to, for example, a GNSS receiver. The trigger signal can initiate GNSS processing (e.g., updating GNSS satellite measurement data) by the GNSS receiver. In some implementations, the predicted time is sent to the GNSS receiver where it is used to set a timer to initiate pedestrian velocity estimation. The periodicity feature can be used by, for example, a GNSS receiver or other systems to affect how and when GNSS satellite data measurements are made or how and when the signals from a GNSS satellite are received and/or processed.

For the sake of generality, the features and processes described herein can also apply to any pedestrian velocity derived at least in part from RF signal processing and RF signal measurements. For example, pedestrian velocity partially derived from WiFi range and/or range rate observations would also benefit from the disclosed implementations. Other examples of RF emitters from which pedestrian velocity can be derived may include but are not limited to, GNSS pseudolites, ranging beacons, cell towers and/or the like.

Example Device Architecture

Figure 5:
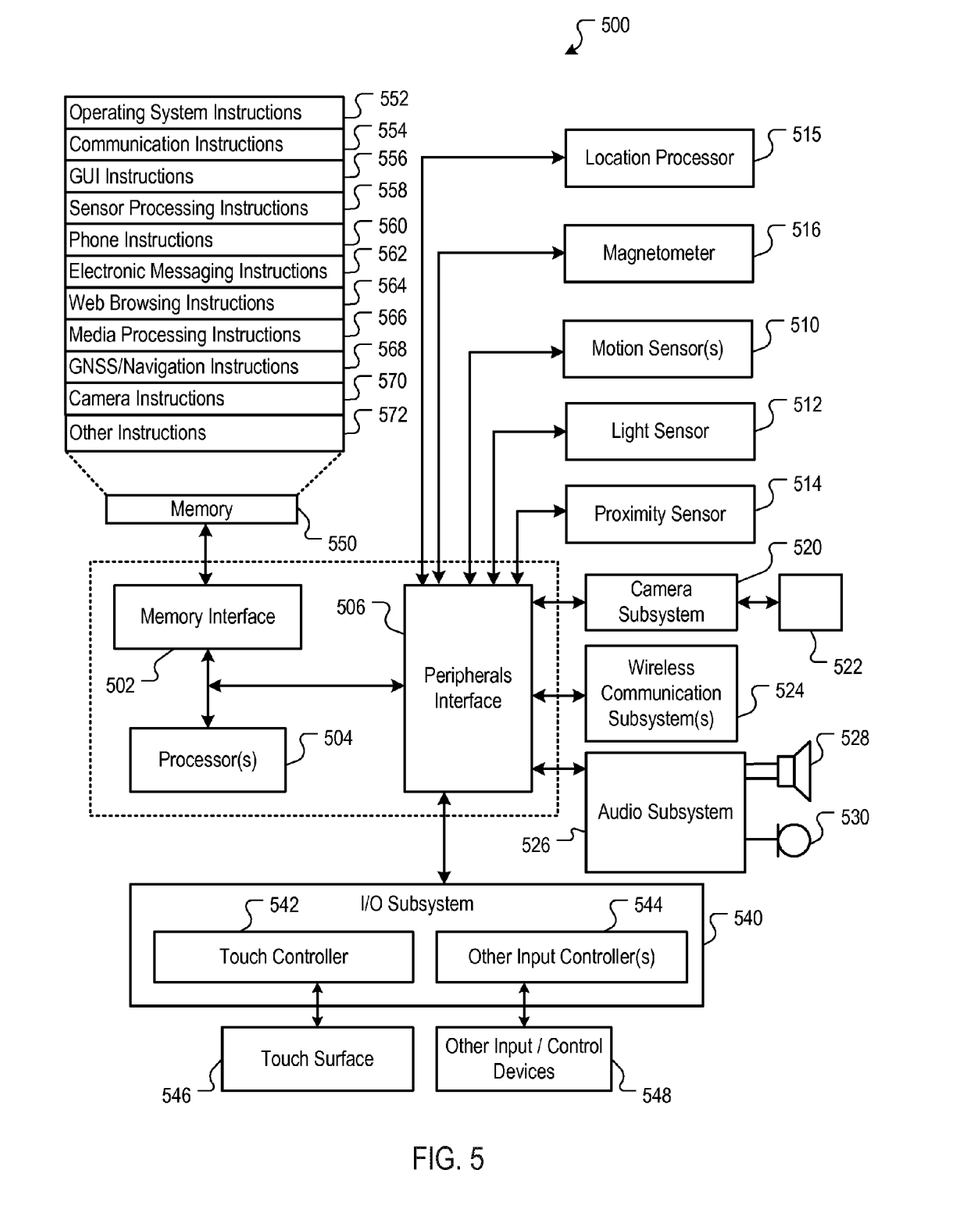
FIG. 5 is a block diagram of example device architecture for implementing the features and processes described in reference to FIGS. 1-4.

FIG. 5 is a block diagram of example device architecture 500 for implementing the features and processes described in reference to FIGS. 1-4. Architecture 500 may be implemented in any mobile device for generating the features and processes described in reference to FIGS. 1-4, including but not limited to portable computers, smart phones, tablet computers, game consoles, wearable computers and the like. Architecture 500 may include memory interface 502, data processor(s), image processor(s) or central processing unit(s) 504, and peripherals interface 506. Memory interface 502, processor(s) 504 or peripherals interface 506 may be separate components or may be integrated in one or more integrated circuits. One or more communication buses or signal lines may couple the various components.

Sensors, devices, and subsystems may be coupled to peripherals interface 506 to facilitate multiple functionalities. For example, motion sensor 510, light sensor 512, and proximity sensor 514 may be coupled to peripherals interface 506 to facilitate orientation, lighting, and proximity functions of the device. For example, in some implementations, light sensor 512 may be utilized to facilitate adjusting the brightness of touch surface 546. In some implementations, motion sensor 510 (e.g., an accelerometer, gyros) may be utilized to detect movement and orientation of the device. Accordingly, display objects or media may be presented according to a detected orientation (e.g., portrait or landscape).

Other sensors may also be connected to peripherals interface 506, such as a temperature sensor, a biometric sensor, or other sensing device, to facilitate related functionalities.

Location processor 515 (e.g., GNSS receiver chip) may be connected to peripherals interface 506 to provide geo-referencing. Electronic magnetometer 516 (e.g., an integrated circuit chip) may also be connected to peripherals interface 506 to provide data that may be used to determine the direction of magnetic North. Thus, electronic magnetometer 516 may be used as an electronic compass.

Camera subsystem 520 and an optical sensor 522, e.g., a charged coupled device (CCD) or a complementary metal-oxide semiconductor (CMOS) optical sensor, may be utilized to facilitate camera functions, such as recording photographs and video clips.

Communication functions may be facilitated through one or more communication subsystems 524. Communication subsystem(s) 524 may include one or more wireless communication subsystems. Wireless communication subsystems 524 may include radio frequency receivers and transmitters and/or optical (e.g., infrared) receivers and transmitters. Wired communication systems may include a port device, e.g., a Universal Serial Bus (USB) port or some other wired port connection that may be used to establish a wired connection to other computing devices, such as other communication devices, network access devices, a personal computer, a printer, a display screen, or other processing devices capable of receiving or transmitting data.

The specific design and implementation of the communication subsystem 524 may depend on the communication network(s) or medium(s) over which the device is intended to operate. For example, a device may include wireless communication subsystems designed to operate over a global system for mobile communications (GSM) network, a GPRS network, an enhanced data GSM environment (EDGE) network, IEEE802.xx communication networks (e.g., Wi-Fi, Wi-Max, ZigBee™), 3G, 4G, 4G LTE, code division multiple access (CDMA) networks, near field communication (NFC), Wi-Fi Direct and a Bluetooth™ network. Wireless communication subsystems 524 may include hosting protocols such that the device may be configured as a base station for other wireless devices. As another example, the communication subsystems may allow the device to synchronize with a host device using one or more protocols or communication technologies, such as, for example, TCP/IP protocol, HTTP protocol, UDP protocol, ICMP protocol, POP protocol, FTP protocol, IMAP protocol, DCOM protocol, DDE protocol, SOAP protocol, HTTP Live Streaming, MPEG Dash and any other known communication protocol or technology.

Audio subsystem 526 may be coupled to a speaker 528 and one or more microphones 530 to facilitate voice-enabled functions, such as voice recognition, voice replication, digital recording, and telephony functions.

I/O subsystem 540 may include touch controller 542 and/or other input controller(s) 544. Touch controller 542 may be coupled to a touch surface 546. Touch surface 546 and touch controller 542 may, for example, detect contact and movement or break thereof using any of a number of touch sensitivity technologies, including but not limited to, capacitive, resistive, infrared, and surface acoustic wave technologies, as well as other proximity sensor arrays or other elements for determining one or more points of contact with touch surface 546. In one implementation, touch surface 546 may display virtual or soft buttons and a virtual keyboard, which may be used as an input/output device by the user.

Other input controller(s) 544 may be coupled to other input/control devices 548, such as one or more buttons, rocker switches, thumb-wheel, infrared port, USB port, and/or a pointer device such as a stylus. The one or more buttons (not shown) may include an up/down button for volume control of speaker 528 and/or microphone 530.

In some implementations, device 500 may present recorded audio and/or video files, such as MP3, AAC, and MPEG video files. In some implementations, device 500 may include the functionality of an MP3 player and may include a pin connector for tethering to other devices. Other input/output and control devices may be used.

Memory interface 502 may be coupled to memory 550. Memory 550 may include high-speed random access memory or non-volatile memory, such as one or more magnetic disk storage devices, one or more optical storage devices, or flash memory (e.g., NAND, NOR). Memory 550 may store operating system 552, such as Darwin, RTXC, LINUX, UNIX, OS X, WINDOWS, or an embedded operating system such as VxWorks. Operating system 552 may include instructions for handling basic system services and for performing hardware dependent tasks. In some implementations, operating system 552 may include a kernel (e.g., UNIX kernel).

Memory 550 may also store communication instructions 554 to facilitate communicating with one or more additional devices, one or more computers or servers, including peer-to-peer communications. Communication instructions 554 may also be used to select an operational mode or communication medium for use by the device, based on a geographic location (obtained by the GPS/Navigation instructions 568) of the device.

Memory 550 may include graphical user interface instructions 556 to facilitate graphic user interface processing, including a touch model for interpreting touch inputs and gestures; sensor processing instructions 558 to facilitate sensor-related processing and functions; phone instructions 560 to facilitate phone-related processes and functions; electronic messaging instructions 562 to facilitate electronic-messaging related processes and functions; web browsing instructions 564 to facilitate web browsing-related processes and functions; media processing instructions 566 to facilitate media processing-related processes and functions; GPS/Navigation instructions 568 to facilitate GPS and navigation-related processes; camera instructions 570 to facilitate camera-related processes and functions; and other instructions 572 for performing some or all of the features and processes, as described in reference to FIGS. 1-4.

Each of the above identified instructions and applications may correspond to a set of instructions for performing one or more functions described above. These instructions need not be implemented as separate software programs, procedures, or modules. Memory 550 may include additional instructions or fewer instructions. Furthermore, various functions of the device may be implemented in hardware and/or in software, including in one or more signal processing and/or application specific integrated circuits (ASICs).

The features described may be implemented in digital electronic circuitry or in computer hardware, firmware, software, or in combinations of them. The features may be implemented in a computer program product tangibly embodied in an information carrier, e.g., in a machine-readable storage device, for execution by a programmable processor; and method steps may be performed by a programmable processor executing a program of instructions to perform functions of the described implementations by operating on input data and generating output.

The described features may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., Objective-C, Java), including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer may communicate with mass storage devices for storing data files. These mass storage devices may include magnetic disks, such as internal hard disks and removable disks; magneto-optical disks; and optical disks. Storage devices suitable for tangibly embodying computer program instructions and data include all forms of non-volatile memory, including by way of example, semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

To provide for interaction with a user the features may be implemented on a computer having a display device such as a CRT (cathode ray tube) or LCD (liquid crystal display) monitor for displaying information to the author, a keyboard and a pointing device, such as a mouse or a trackball by which the author may provide input to the computer.

The features may be implemented in a computer system that includes a back-end component, such as a data server or that includes a middleware component, such as an application server or an Internet server, or that includes a front-end component, such as a client computer having a graphical user interface or an Internet browser, or any combination of them. The components of the system may be connected by any form or medium of digital data communication such as a communication network. Examples of communication networks include a LAN, a WAN and the computers and networks forming the Internet.

The computer system may include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an Application Programming Interface (API). An API may define on or more parameters that are passed between a calling application and other software code (e.g., an operating system, library routine, function) that provides a service, that provides data, or that performs an operation or a computation.

The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer will employ to access functions supporting the API.

In some implementations, an API call may report to an application the capabilities of a device running the application, such as input capability, output capability, processing capability, power capability, communications capability, etc.

As described above, some aspects of the subject matter of this specification include gathering and use of data available from various sources to improve services a mobile device can provide to a user. The present disclosure contemplates that in some instances, this gathered data may identify a particular location or an address based on device usage. Such personal information data can include location-based data, addresses, subscriber account identifiers, or other identifying information.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

In the case of advertisement delivery services, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are operable even if they lack all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

A number of implementations have been described. Nevertheless, it will be understood that various modifications may be made. Elements of one or more implementations may be combined, deleted, modified, or supplemented to form further implementations. In yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method comprising:
generating, by one or more motion sensors of a mobile device, a periodic sensor signal in response to periodic motion of the mobile device caused by a user's arm swing;
receiving, by a processor of the mobile device, the periodic sensor signal;
determining, by the processor, a fundamental motion frequency of the periodic sensor signal using a sliding window Discrete Fourier Transform (DFT), where length of the sliding window is approximately equal to a fundamental period of the user's arm swing, and lowest non-zero frequency bin output by the DFT is selected as the fundamental motion frequency;
extracting, by the processor, a periodicity feature from the periodic sensor signal based on the fundamental motion frequency;
responsive to the extracting, configuring a global navigation satellite system (GNSS) receiver of the mobile device to estimate GNSS velocity of the GNSS receiver; and
displaying, by the mobile device, the user's speed or distance traveled based on the estimated GNSS velocity.

2. The method of claim 1, wherein the periodic sensor signal is acceleration magnitude and the periodicity feature is minimum acceleration magnitude.

3. The method of claim 1, further comprising:
tracking a phase of the periodic sensor signal based on the fundamental motion frequency.

4. The method of claim 3, where the phase is tracked using a Kalman filter.

5. The method of claim 1, where the received periodic sensor signal is pre-processed by a moving average or moving median filter.

6. A mobile device comprising:
one or more motion sensors configured to generate a periodic sensor signal in response to periodic motion of the mobile device caused by a user's arm swing;
a display;
a global navigation satellite system (GNSS) receiver;
one or more processors;
one or more computer-readable mediums coupled to the one or more processors and configured to store instructions, that when executed by the one or more processors, cause the one or more processors to perform operations comprising:
determining a fundamental motion frequency of the periodic sensor signal using a sliding window Discrete Fourier Transform (DFT), where length of the sliding window DFT is approximately equal to a fundamental period of the user's arm swing, and lowest non-zero frequency bin output by the DFT is selected as the fundamental motion frequency;
extracting a periodicity feature from the periodic sensor signal based on the fundamental motion frequency;
responsive to the extracting, configuring the GNSS receiver to estimate GNSS velocity of the GNSS receiver; and displaying, by the display, the user's speed or distance traveled based on the estimated GNSS velocity.

7. The mobile device of claim 6, wherein the periodic sensor signal is acceleration magnitude and the periodicity feature is minimum acceleration magnitude.

8. The mobile device of claim 6, further comprising:
tracking a phase of the periodic sensor signal based on the fundamental motion frequency.

9. The mobile device of claim 8, where the phase is tracked using a Kalman filter.

10. The mobile device of claim 6, where the received periodic sensor signal is pre-processed by a moving average or moving median filter.

11. A non-transitory, computer-readable storage medium having instructions stored thereon, that when executed by one or more processors of a mobile device, cause the one or more processors to perform operations comprising:
receiving a periodic sensor signal generated by one or more motion sensors of the mobile device in response to periodic motion of the mobile device caused by a user's arm swing;
determining, by the one or more processor of the mobile device, a fundamental motion frequency of the periodic sensor signal using a sliding window Discrete Fourier Transform (DFT), where length of the sliding window is approximately equal to a fundamental period of the user's arm swing, and lowest non-zero frequency bin output by the DFT is selected as the fundamental motion frequency;
extracting, by the one or more processor, a periodicity feature from the periodic sensor signal based on the fundamental motion frequency;
responsive to the extracting, configuring a GNSS receiver of the mobile device to estimate initiating pedestrian velocity estimation GNSS velocity of the GNSS receiver; and
displaying, by a display of the mobile device, the user's speed or distance traveled based on the estimated GNSS velocity.

12. The non-transitory, computer-readable storage medium of claim 11, wherein the periodic sensor signal is acceleration magnitude and the periodicity feature is minimum acceleration magnitude.

13. The non-transitory, computer-readable storage medium of claim 11, further comprising:
tracking a phase of the periodic sensor signal based on the fundamental motion frequency.

14. The non-transitory, computer-readable storage medium of claim 13, where the phase is tracked using a Kalman filter.

15. The non-transitory, computer-readable storage medium of claim 11, where the received periodic sensor signal is pre-processed by a moving average or moving median filter.

* * * * *